(12) United States Patent
Gliner et al.

(10) Patent No.: US 10,638,932 B2
(45) Date of Patent: May 5, 2020

(54) MRI THERMOGRAPHY FOR CARDIAC LESION ASSESSMENT

(71) Applicant: BIOSENSE WEBSTER (ISRAEL) LTD., Yokneam (IL)

(72) Inventors: Vadim Gliner, Haifa (IL); Alon Boumendil, Givat Nili (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 672 days.

(21) Appl. No.: 15/346,901

(22) Filed: Nov. 9, 2016

(65) Prior Publication Data

US 2018/0125367 A1    May 10, 2018

(51) Int. Cl.
| | | |
|---|---|---|
| A61B 5/05 | (2006.01) |
| A61B 5/00 | (2006.01) |
| G01R 33/567 | (2006.01) |
| A61B 5/06 | (2006.01) |
| G01R 33/48 | (2006.01) |
| A61B 5/01 | (2006.01) |

(Continued)

(52) U.S. Cl.
CPC ............ *A61B 5/0044* (2013.01); *A61B 5/015* (2013.01); *A61B 5/055* (2013.01); *A61B 5/066* (2013.01); *A61B 5/7214* (2013.01); *A61B 18/1492* (2013.01); *G01R 33/285* (2013.01); *G01R 33/4804* (2013.01); *G01R 33/567* (2013.01); *G01R 33/5673* (2013.01); *A61B 2018/00351* (2013.01); *A61B 2018/00577* (2013.01); *A61B 2018/00791* (2013.01); *A61B 2018/00839* (2013.01); *A61B 2034/2051* (2016.02); *A61B 2090/374* (2016.02); *A61B 2576/023* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |

(Continued)

FOREIGN PATENT DOCUMENTS

| | | |
|---|---|---|
| WO | WO 2012/145285 A1 | 10/2012 |
| WO | WO 2012/170119 A1 | 12/2012 |

OTHER PUBLICATIONS

Volland, N. A. et al., "Limited FOV MR thermometry using a local cardiac RF coil in atrial fibrillation treatment", Proc. Intl. Soc. Mag. Reson. Med., (2011) p. 1764, 19.

(Continued)

*Primary Examiner* — Joel F Brutus

(57) ABSTRACT

Described embodiments include an apparatus that includes an electrical interface and a processor. The processor is configured to receive via the electrical interface, from a plurality of sensors, a first signal that indicates a location of an intrabody tool inside a body of a subject, and a second signal that indicates a phase, of a physiological motion cycle of the subject, at which the first signal was acquired. The processor is further configured to acquire, using a magnetic resonance imaging (MRI) scanner, a set of multiple images at the location indicated by the first signal, over a portion, of a subsequent physiological motion cycle of the subject, that includes the phase indicated by the second signal. Other embodiments are also described.

20 Claims, 3 Drawing Sheets

(51) Int. Cl.
*A61B 5/055* (2006.01)
*A61B 18/14* (2006.01)
*G01R 33/28* (2006.01)
*A61B 90/00* (2016.01)
*A61B 34/20* (2016.01)
*A61B 18/00* (2006.01)

(56) References Cited

U.S. PATENT DOCUMENTS

| | | |
|---|---|---|
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 8,801,701 B2 | 8/2014 | Chopra et al. |
| 8,942,781 B2 | 1/2015 | Carpentier et al. |
| 9,028,470 B2 | 5/2015 | Marrouche |
| 2002/0065455 A1* | 5/2002 | Ben-Haim ......... A61N 1/36564 600/407 |
| 2004/0039293 A1* | 2/2004 | Porath ................. A61B 5/0422 600/509 |
| 2008/0146912 A1 | 6/2008 | Richard et al. |
| 2010/0061597 A1* | 3/2010 | Kanda .................... A61B 1/041 382/107 |
| 2010/0222671 A1* | 9/2010 | Cohen ................. A61B 5/0044 600/424 |
| 2010/0312096 A1* | 12/2010 | Guttman ............... A61B 5/415 600/411 |
| 2011/0046475 A1* | 2/2011 | Assif ..................... G01R 33/24 600/422 |
| 2011/0164126 A1* | 7/2011 | Ambor ................. A61B 1/0005 348/65 |
| 2015/0099965 A1 | 4/2015 | Volland et al. |

OTHER PUBLICATIONS

Yuan, J. et al., "Towards fast and accurate temperature mapping with proton resonance frequency-based MR thermometry", Quant Imaging Med. Surg., Jan. 26, 2012, DOI:10.3978/j.issn.2223-4292. 2012.01.06.

European Search Report dated Mar. 23, 2018 from corresponding European Patent Application No. 17200635.5.

* cited by examiner

MRI THERMOGRAPHY FOR CARDIAC LESION ASSESSMENT

FIELD OF THE INVENTION

The present invention relates to magnetic resonance imaging (MRI), especially as applied interventionally, to guide a procedure.

BACKGROUND

In a cardiac ablation procedure, radiofrequency energy may be delivered to arrhythmia-causing cardiac tissue, thus causing lesions in this tissue that render the tissue electrically inactive.

Magnetic resonance imaging (MRI) is an imaging technique that acquires complex-valued signals, which may be processed, and used, in various ways. For example, the magnitude of such a complex-valued signal may be computed, to produce a "magnitude image" for viewing by a radiologist. Alternatively or additionally, the phase of such a complex-valued signal may be computed, to produce a "phase image." Such a phase image may be used, for example, for MRI thermography (or "MRI thermometry"), a technique by which tissue temperature is measured. In one variation of this technique, for example, changes in temperature are derived from differences in image phase. Thus, for example, if a reference image of a particular portion of tissue, acquired at a first time, has the phase $\phi_0$, and a subsequent image of the same portion of tissue, acquired at a second time, has a different phase $\phi_1$, the change in temperature of the portion of tissue between the first and second times may be derived from the difference $\phi_1 - \phi_0$. MRI thermography may be used to provide a temperature map of the tissue area of interest; hence, MRI thermography may be alternatively referred to as "MRI-based temperature mapping."

Yuan, Jing, et al., "Towards fast and accurate temperature mapping with proton resonance frequency-based MR thermometry," Quantitative imaging in medicine and surgery 2.1 (2012): 21-32, reviews the basic principles of proton resonance frequency (PRF) thermometry, and further discusses technical advancements aimed at increasing the imaging speed and/or temperature accuracy of PRF-based thermometry sequences, such as image acceleration, fat suppression, reduced field-of-view imaging, as well as motion tracking and correction.

Volland, N A, et al., Limited FOV MR thermometry using a local cardiac RF coil in atrial fibrillation treatment," Proc. Intl. Soc. Mag. Reson. Med. 19 (2011): 1764, investigates the development of a local RF heart coil that would allow the acquisition of coil-sensitivity limited field of view (FOV) MR lesion or temperature images in less than 200 ms per image with high sensitivity.

US Patent Application Publication 2015/0099965, whose disclosure is incorporated herein by reference, describes a catheter-mounted, expandable or set in position, coil for magnetic resonance imaging. The coil has a catheter sheath including an elongated tube with a central axis, the catheter sheath having an opening at an end thereof; an expandable coil including a conductive material connected to an expansion mechanism which, when deployed, maintains the expandable receive coil shape; and a cable running through the catheter sheath, the cable being electrically connected to the coil inductive loop.

SUMMARY OF THE INVENTION

There is provided, in accordance with some embodiments of the present invention, apparatus that includes an electrical interface and a processor. The processor is configured to receive via the electrical interface, from a plurality of sensors, a first signal that indicates a location of an intrabody tool inside a body of a subject, and a second signal that indicates a phase, of a physiological motion cycle of the subject, at which the first signal was acquired. The processor is further configured to acquire, using a magnetic resonance imaging (MRI) scanner, a set of multiple images at the location indicated by the first signal, over a portion, of a subsequent physiological motion cycle of the subject, that includes the phase indicated by the second signal.

In some embodiments, the first signal further indicates an orientation of the intrabody tool, and the processor is configured to acquire the set of images along the orientation of the intrabody tool.

In some embodiments, the portion of the subsequent motion cycle is temporally centered on the phase indicated by the second signal.

In some embodiments, the motion cycle is a cardiac cycle, and the subsequent motion cycle is a subsequent cardiac cycle.

In some embodiments, the intrabody tool includes an ablation catheter, and the processor is configured to acquire the set of images while the ablation catheter is ablating a portion of cardiac tissue.

In some embodiments, the portion of the subsequent cardiac cycle has a duration of 70-130 ms.

In some embodiments, the set of images includes between 10 and 20 images.

In some embodiments, the processor is configured to acquire a plurality of sets of images over, respectively, a plurality of subsequent physiological motion cycles of the subject.

In some embodiments, the processor is further configured to select, from the set, an image that shows the intrabody tool better than other images of the set, by matching a template image, which shows the intrabody tool, to the set of images.

In some embodiments, the processor is further configured to update a temperature map, using a phase image that corresponds to the selected image.

There is further provided, in accordance with some embodiments of the present invention, a method that includes receiving, from a plurality of sensors, a first signal that indicates a location of an intrabody tool inside a body of a subject, and a second signal that indicates a phase, of a physiological motion cycle of the subject, at which the first signal was acquired. The method further includes, using a magnetic resonance imaging (MRI) scanner, acquiring a set of multiple images at the location indicated by the first signal, over a portion, of a subsequent physiological motion cycle of the subject, that includes the phase indicated by the second signal.

The present invention will be more fully understood from the following detailed description of embodiments thereof, taken together with the drawings, in which:

DETAILED DESCRIPTION OF EMBODIMENTS

Overview

Figure 1:
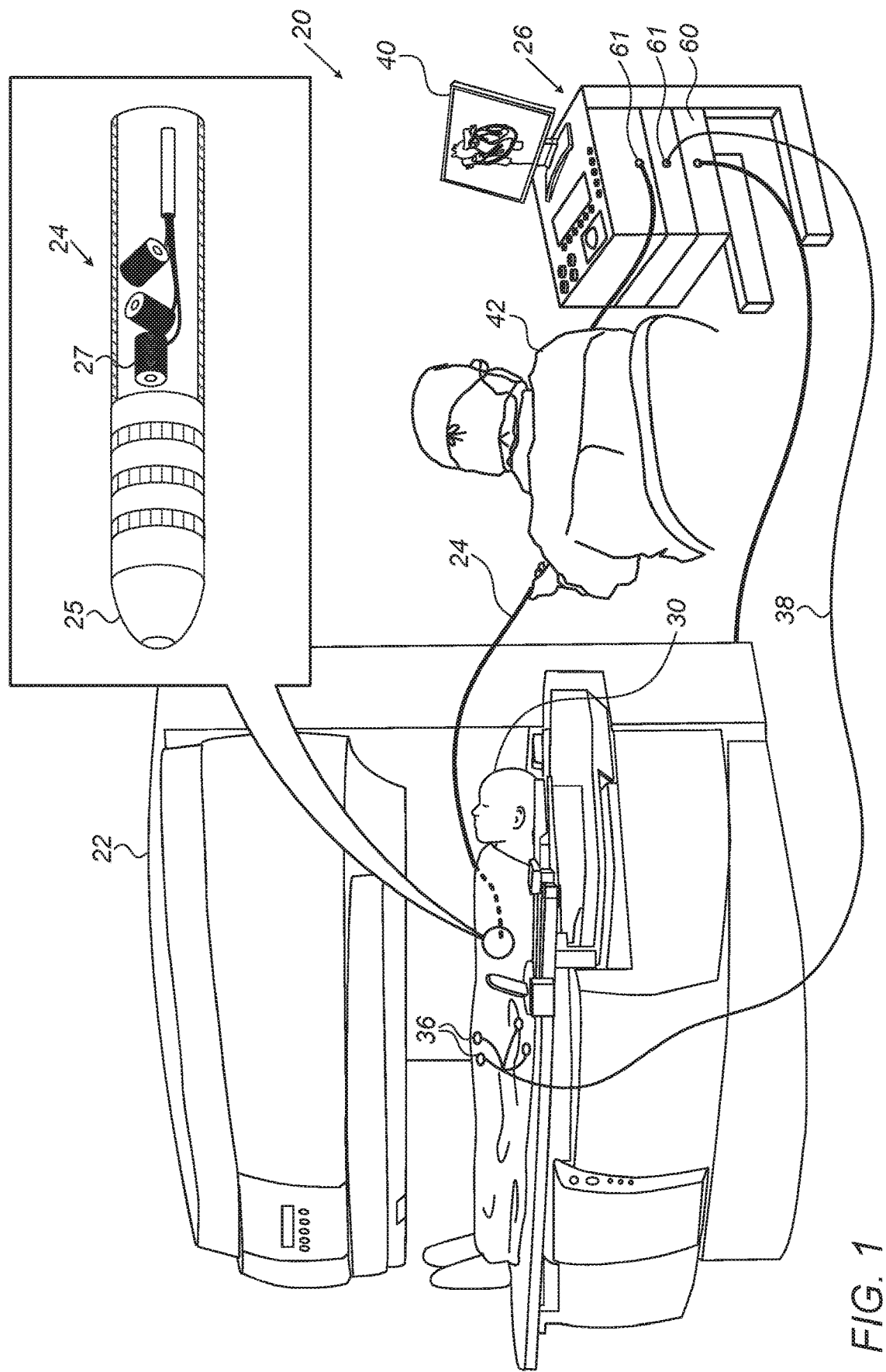
FIG. 1 is a schematic illustration of an MRI-guided ablation system, in accordance with some embodiments of the present invention.

While performing a cardiac ablation on a subject, it may be helpful to measure the temperature of the ablated tissue (i.e., the lesion), such as to facilitate tracking the progression of the procedure. MRI thermography is an accurate method of measuring temperature. However, due to movement of the heart, it may be challenging for the MRI scanner to track the ablated tissue.

One option is to acquire an image (or "slice") at a particular location, at a particular phase in the cardiac cycle at which the ablated portion of tissue is expected to be at the particular location. In other words, the field-of-view (FOV) of the MRI scanner may be set to the particular location, and the image acquisition may be gated to the particular phase, such that a single MRI image is acquired, per cardiac cycle, at the particular location and phase. A drawback to this technique, however, is that the motion of the heart may exhibit variation from one cycle to the next, such that the location of the ablated tissue, at the particular phase, varies between cycles. Moreover, the ablation catheter may be intentionally moved, or may slip unintentionally, such that the MRI scanner ceases to capture the ablated tissue.

Another option is to perform rapid, ungated MRI imaging over the full cardiac cycle, at a particular location or at several locations, and to extract, from the full set of acquired images, the images that best show the ablated tissue. This technique is more likely than the previously-described technique to capture the ablated tissue, at least for some of the cardiac cycles during which the imaging is performed. However, since the ablated tissue is shown in only a small fraction of the acquired images, a large amount of processing is needed to separate the small number of images of interest from the large number of irrelevant images. This need for extensive processing renders the technique difficult to implement, and generally impractical for real-time temperature mapping.

Embodiments of the present invention therefore provide a superior technique for imaging the ablated tissue. Per this technique, the ablation catheter is equipped with sensors, such as electromagnetic sensors belonging to a magnetic tracking system, which track the location of the catheter, and hence, also track the location of the tissue that is currently being ablated. The tracked location is fed to the processor that controls the MRI scanner, such that the MRI scanner can "follow" the catheter in the event that the catheter moves to a different portion of tissue. To compensate for intra-cycle movement of the heart, as well as inter-cycle variations in such movement, a "partial gating" technique is performed, whereby rapid MRI imaging is performed during a portion of the cardiac cycle that is approximately temporally centered around the phase of the cardiac cycle at which the catheter location was obtained. For example, assuming the catheter's location was measured at the R peak of the subject's echocardiogram (ECG) during the previous cardiac cycle, the MRI scanner may acquire, during the current cardiac cycle, a set of 10-20 images at the measured location, over a period of 70-130 ms that is approximately centered around the R peak. (For example, the image acquisition may begin 50 ms before the R peak, and continue until 50 ms after the R peak.) In this manner, the ablated tissue has a high probability of appearing in at least one of the images acquired during each cardiac cycle, yet the number of acquired images is not overly large, since the acquisition of images takes place only over a portion of the cardiac cycle.

Typically, a template image that shows the catheter is correlated with each acquired set of images, in order to automatically find the image that best shows the catheter. In other words, each set of images is automatically filtered, such that only the image having the best correlation with the template image is selected. Since the size of each set is relatively small, this filtering may be performed relatively quickly, and generally in real-time. Subsequently, the phase image corresponding to the selected image is used to update the temperature map.

It is noted that the term "image," as used in the claims and description of the present application, may refer to the "raw" complex-valued image data acquired from a scan, or to an image derived therefrom. Typically, if not preceded by a modifier, the term "image" refers either to the raw complex-valued image data, or to a derived image, such as a magnitude image, that is used to visually represent the imaged tissue. The term "phase image," on the other hand, as described above, refers to the image obtained by computing the phase of the received image data. For example, assuming the MRI scan returns a two-dimensional matrix of complex values A+iB, the "image" may include a matrix of the same dimensions, having the values $\sqrt{(A^2+B^2)}$, while the corresponding phase image may include a matrix of the same dimensions, having the values $$\tan^{-1}\left(\frac{B}{A}\right).$$

(The "image phase," or the term "phase" as used in the context of a phase image, should not be confused with the term "cardiac phase," or the term "phase" as used in the context of a physiological motion cycle.)

System Description

Reference is initially made to FIG. 1, which is a schematic illustration of an MRI-guided ablation system 20, in accordance with some embodiments of the present invention.

System 20 comprises an MRI scanner 22, configured to image a subject 30 while a physician 42 performs an ablation procedure on the subject. System 20 further comprises a processor 60, located, for example, in a console 26. During the procedure, processor 60 controls the image acquisition by the MRI scanner, as described in detail hereinbelow.

To perform the ablation, physician 42 uses an ablation catheter 24. Typically, catheter 24 comprises one or more ablation electrodes 25, and further comprises one or more tracking sensors 27, which output tracking signals that indicate the location, and orientation, of the catheter inside the body of the subject. For example, each tracking sensor 27 may comprise a coil. During the procedure, one or more magnetic-field generators (not shown) may generate magnetic fields, at different frequencies from those generated by the MRI scanner, which induce voltages in the coils. These induced voltages are received, by the processor, via an electrical interface 61. (Electrical interface 61 may comprise, for example, a port or socket, situated, for example, anywhere on the surface of, or inside, console 26.) Based on the induced voltages, the processor ascertains the location and orientation of the catheter. Such magnetic tracking techniques are described, for example, in U.S. Pat. Nos. 5,391,199, 5,443,489, 6,788,967, 6,690,963, 5,558,091, 6,172,499, and 6,177,792, whose disclosures are incorporated herein by reference.

Alternatively or additionally, system 20 may comprise any other types of sensors, which may be used to implement any other suitable tracking technique for tracking the location and/or orientation of the catheter. For example, impedance sensors may be used to implement an impedance-based tracking technique, as described, for example, in U.S. Pat. Nos. 5,983,126, 6,456,864 and 5,944,022, whose disclosures are incorporated herein by reference.

System 20 further comprises one or more physiological sensors 36, which output signals that indicate the phase of the cardiac cycle of the subject at which the tracking signals were acquired. For example, as shown in the figure, physiological sensors 36 may comprise one or more conductive patches that function as ECG sensors, in that, when coupled to the body of the subject, these conductive patches acquire ECG signals from the subject. These ECG signals are conveyed, via a cable 38 and an electrical interface 61, to processor 60. Alternatively or additionally, processor 60 may receive intracardiac ECG signals, acquired by ECG sensors in catheter 24.

During the procedure, images acquired by the MRI scanner, and/or temperature maps derived therefrom, may be displayed on a display 40, to help guide the procedure.

In general, processor 60 may be embodied as a single processor, or a cooperatively networked or clustered set of processors. Processor 60 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2:
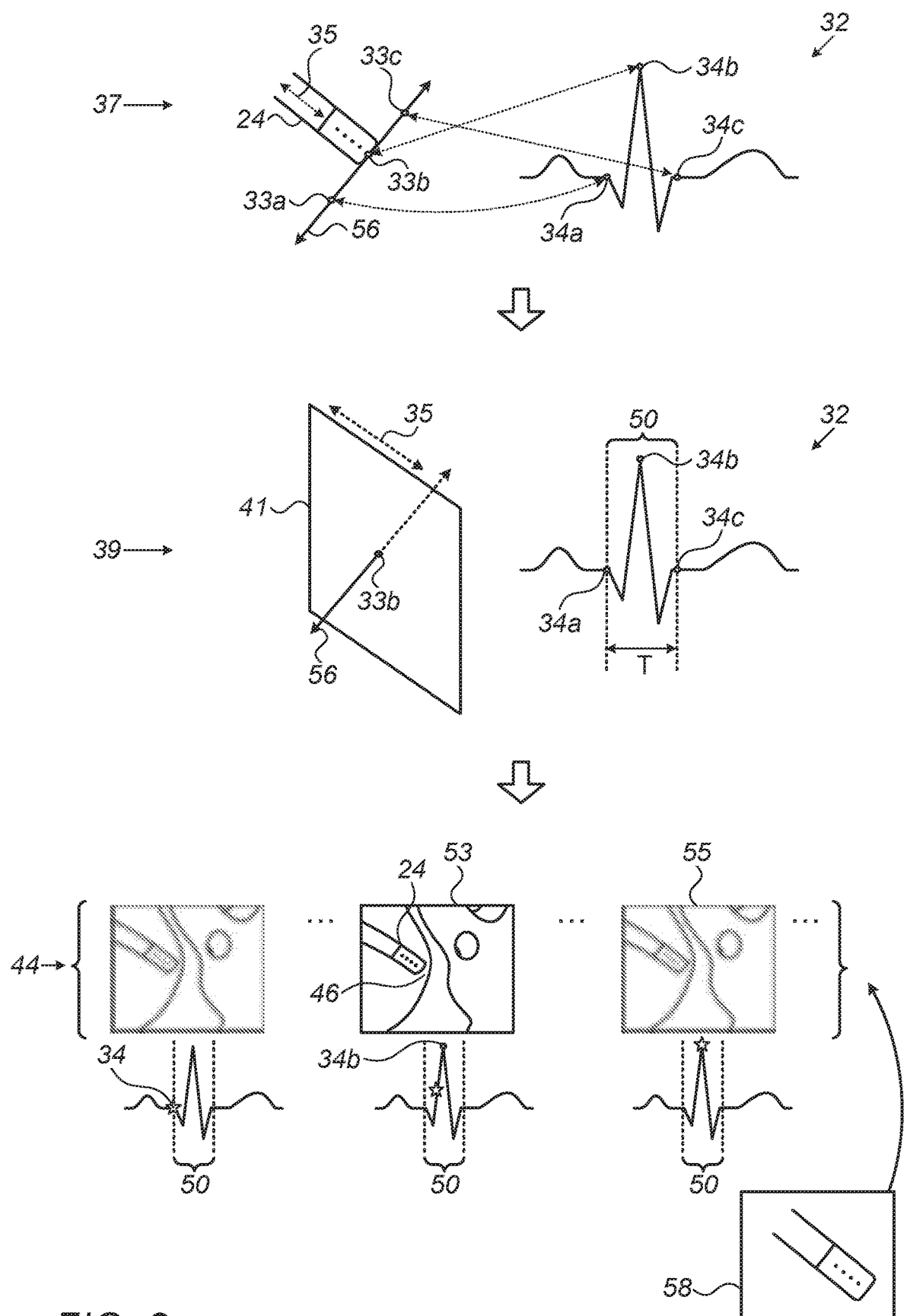
FIG. 2 is a schematic illustration of a technique for acquiring a set of MRI images, in accordance with some embodiments of the present invention.

Reference is now made to FIG. 2, which is a schematic illustration of a technique for acquiring a set of MRI images, in accordance with some embodiments of the present invention.

The top portion 37 of FIG. 2 illustrates the manner in which the location and/or orientation of catheter 24 may vary over the course of a cardiac cycle. A bidirectional arrow 56, with several location markers, indicates the pathway that the catheter may follow, and an ECG signal 32 is marked to show the respective cardiac phases that correspond to these location markers. In particular, the distal tip of the catheter is assumed to be at location 33a at phase 34a, at location 33b at phase 34b, and at location 33c at phase 34c. The orientation 35 of the catheter (which may be defined, for example, as the orientation of the central longitudinal axis of the catheter) may also vary, over the course of the cardiac cycle. As described above, each location and orientation is received from tracking sensors 27, while each ECG signal 32 is received from physiological sensors 36.

Typically, physician 42 selects a suitable phase of the cardiac cycle around which to acquire MRI images. For example, the physician may choose the R peak, which, in FIG. 2, is phase 34b. As shown in the second portion 39 of the figure, processor 60 then sets the imaging parameters in accordance with this selection. For example, the processor may define an MRI scan plane 41 that passes through (e.g., is centered at) location 33b, which is the location corresponding to the selected phase 34b. (In other words, the processor sets the FOV of the scanner to include location 33b.) Typically, the processor defines scan plane 41 such that the scan plane also has orientation 35; this facilitates showing the catheter "in plane." Additionally, the processor defines a scan window, which covers a portion 50 of the cardiac cycle that includes (e.g., is temporally centered at) phase 34b. The processor further defines the number of images to be acquired during this scan window, and/or the duration between the acquisitions of successive images.

Subsequently, as indicated in the bottom portion of FIG. 2, the processor drives MRI scanner 22 to acquire a set 44 of images during a subsequent cardiac cycle, in accordance with the imaging parameters. In other words, set 44 is acquired at location 33b, and typically also along orientation 35, over portion 50 of the subsequent cardiac cycle. FIG. 2 shows several images from set 44, each of which was acquired at a different phase of portion 50 of the cardiac cycle, as indicated by a marker 34 in the ECG-signal icons beneath these images.

As described above, an advantage of acquiring a set 44 of images—rather than a single image gated to phase 34b—is that acquiring the set of images increases the likelihood of imaging the catheter, and hence, the ablated portion of tissue. In particular, as described above, the heart may exhibit inter-cycle variations in movement, and/or the catheter may move slightly with respect to the heart, such that, if only a single image were acquired at phase 34b, the catheter might be missed. Due, however, to the multiple images acquired at various phases within the scan window, it is likely that at least one of the acquired images will show the catheter. For example, in the case shown in FIG. 2, the catheter, and the ablated portion 46 of tissue, are not shown clearly in an image 55, which was acquired at phase 34b, but are instead shown clearly in an image 53, which was acquired before phase 34b. Hence, if not for the acquisition of image 53, the catheter would have been missed.

To facilitate "catching" the catheter in at least one image, the duration T of the scan window, and the number of images acquired during this scan window, are large enough to compensate for any inter-cycle variation in the movement of the heart, and for any small changes in the position of the catheter relative to the heart. For example, duration T may be between 70 and 130 ms long, and/or the number N of images included in set 44, which is acquired over duration T, may be between 10 and 20 images. With an appropriate selection of T and N, catheter 24 is likely to pass through scan plane 41, while at least one of the images is acquired. (Nonetheless, as described above, N is not prohibitively large, such that each set of images may be processed in real-time.)

Typically, a plurality of sets 44 of images are acquired, respectively, over a plurality of (typically consecutive) cardiac cycles, while the ablation catheter is ablating portion 46 of cardiac tissue. Typically, the scan-plane location and orientation, and the cardiac phase around which the partial gating is performed, are not changed, unless a significant change in the catheter's location and/orientation is observed. In some embodiments, the processor computes the difference in location and/or orientation, and resets the scan parameters if this difference exceeds a threshold. For example, if, during the R peak of a first heartbeat, the catheter was at location (x0, y0, z0), and, during the R peak of a subsequent heartbeat, the catheter is at (x1, y1, z1), the processor may compare the displacement $\sqrt{(x1-x0)^2+(y1-y0)^2+(z1-z0)^2}$ to a threshold. If this displacement exceeds the threshold, the processor may move the scan plane to location (x1, y1, z1).

(In general, the catheter may be intentionally moved during the ablation procedure, to ablate a different portion of tissue, or the catheter may slip.)

After acquiring each set 44 of images, processor 60 typically processes the set in real-time, such as to select the image in the set that best shows the catheter (i.e., that shows the catheter better than other images of the set). Typically, the processor matches a template image 58, which shows the catheter, to the set of images, and the image having the best match with template image 58 is selected. (Template image 58 is typically acquired in advance of the procedure.) Typically, in performing this match, the processor calculates the cross-correlation between template image 58 and each of the images in set 44, and selects the image with the highest cross-correlation. For example, with reference to the example shown in FIG. 2, the processor may select image 53.

Subsequently, the processor may use the phase image that corresponds to the selected image to update the temperature map of the tissue. Typically, this update is performed only if the cross-correlation of the selected image with the template image exceeds a threshold, indicating that the catheter is clearly shown in the selected image. (As noted above, an image that clearly shows the catheter will also, typically, clearly show the ablated tissue, such that the phase image that corresponds to this image is suitable for updating the temperature map.) In the event that the cross-correlation does not exceed the threshold, indicating that the catheter is not clearly shown, the processor does not update the temperature map, but instead moves on to the next set of images.

Since the above-described processing is performed in real-time, the temperature map may help guide the ablation procedure. For example, the physician may decide to terminate the procedure, if the temperature map shows a sufficiently-high tissue temperature.

Figure 3:
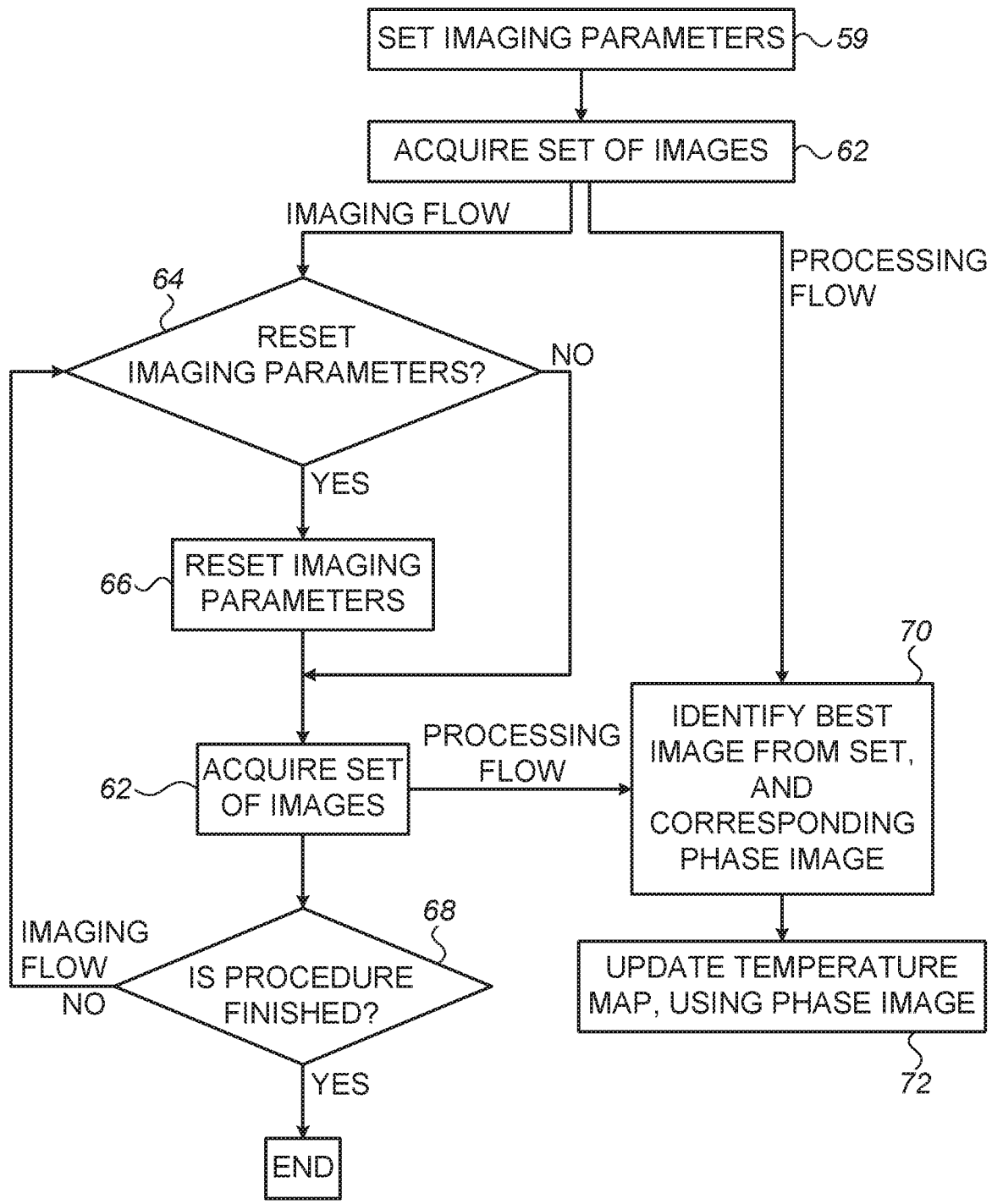
FIG. 3 is a flow diagram for a method for imaging a subject during a cardiac ablation procedure, in accordance with some embodiments of the present invention.

Reference is now made to FIG. 3, which is a flow diagram for a method, performed by system 20 as described above, for imaging a subject during a cardiac ablation procedure, in accordance with some embodiments of the present invention.

First, at a parameter-setting step 59, the processor sets the imaging parameters. (As described above, at least some of these parameters, such as the scan-plane location and orientation, and the scan window, are based on the received sensor signals.) MRI scanner 22 then acquires, at an image-acquiring step 62, a first set of images, in accordance with these parameters. System 20 then performs two flows of operation, typically in parallel: in an imaging flow, system 20 continues to image the subject, while in a processing flow, the system processes the acquired set of images, and updates a temperature map accordingly. Similarly, after each subsequent acquisition of a set of images, the processing flow is performed for the newly-acquired set, and, if the ablation procedure is not yet finished, the imaging flow is also performed, typically in parallel to the processing flow. Each of these flows will now be described.

(i) Imaging Flow

First, at a parameter-checking step 64, the processor checks if the imaging parameters should be reset. For example, as described above, the processor may check if the most recent tracking signal indicates that the catheter has moved to a new location. If the processor determines that the parameters should be reset, the processor resets the parameters, at a parameter-resetting step 66. The processor then acquires the next set of images, at image-acquiring step 62. After acquiring this set of images, the processor checks, at a checking step 68, whether the ablation procedure is finished. (Typically, the processor is connected to the radiofrequency (RF) generator that generates the ablation signals, such that the processor may check whether the ablation procedure is finished by checking whether the RF generator is running.) If the procedure is not yet finished, the processor returns to parameter-checking step 64.

(ii) Processing Flow

For each acquired set of images, the processor identifies, at an image-identifying step 70, the image from the set that best shows the catheter. (As described above, this is typically performed by matching a template to the images in the set.) The processor also identifies the phase image that corresponds to this "best" image. The processor then uses this phase image to update the temperature map, at an updating step 72.

As described above, the number of images in each acquired set is typically not too large, such that the set may be processed relatively quickly. For example, each set may be processed before the end of, or even before the beginning of, the acquisition of the next set. Thus, the temperature map may be updated rapidly, in real-time.

In some embodiments, processor 60 is configured to perform multiple tasks on multiple respective threads, such as to facilitate the parallel performance of the two flows of operation. Thus, for example, the processor may perform parameter-checking step 64 on a first thread, while performing image-identifying step 70 on a second thread.

Although the above description relates mainly to cardiac ablation procedures, it is noted that the principles described herein may be applied to any suitable procedure in which an intrabody tool moves, within any portion of the body, with a physiological motion cycle, such as a cardiac or respiratory motion cycle, of a subject. Moreover, the principles described herein may be applied even outside the context of MRI thermography, in that each acquired set of images may be processed for any suitable purpose.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus for improving ablation tracking, comprising:
an electrical interface; and
a processor, configured:
to receive via the electrical interface, from a plurality of sensors, a first signal that indicates a location and orientation of an intrabody tool inside a body of a subject, and a second signal that indicates a phase; of a physiological motion cycle of the subject, at which the first signal was acquired, and to acquire, using a magnetic resonance imaging (MRI) scanner, a set of multiple images at the location indicated by the first signal, over a portion, of a subsequent physiological motion cycle of the subject, that includes the phase indicated by the second signal, the processor defining a scan plane covering a pathway of the intrabody tool, a scan window that covers a portion of the physiological motion cycle that is approximately temporally centered around the phase of the physiological motion cycle at the location and orientation of the intrabody tool, and a number of images to be captured in the scan window, the set of multiple images are captured at various phases within the scan window.

2. The apparatus according to claim 1, wherein the first signal further indicates an orientation of the intrabody tool, and wherein the processor is configured to acquire the set of multiple images along the orientation of the intrabody tool.

3. The apparatus according to claim 1, wherein the portion of the subsequent motion cycle is temporally centered on the phase indicated by the second signal.

4. The apparatus according to claim 1, wherein the motion cycle is a cardiac cycle, and the subsequent motion cycle is a subsequent cardiac cycle.

5. The apparatus according to claim 4, wherein the intrabody tool includes an ablation catheter, and wherein the processor is configured to acquire the set of multiple images while the ablation catheter is ablating a portion of cardiac tissue.

6. The apparatus according to claim 4, wherein the portion of the subsequent cardiac cycle has a duration of 70-130 ms.

7. The apparatus according to claim 1, wherein the set of multiple images includes between 10 and 20 images.

8. The apparatus according to claim 1, wherein the processor is configured to acquire a plurality of sets of images over, respectively, a plurality of subsequent physiological motion cycles of the subject.

9. The apparatus according to claim 1, wherein the processor is further configured to select, from the set, a selected image that shows the intrabody tool better than other images of the set, by matching a template image, which shows the intrabody tool, to the set of multiple images.

10. The apparatus according to claim 9, wherein the processor is further configured to update a temperature map, using a phase image that corresponds to the selected image.

11. A method for improving ablation tracking, comprising: receiving, from a plurality of sensors, a first signal that indicates a location and orientation of an intrabody tool inside a body of a subject, and a second signal that indicates a phase, of a physiological motion cycle of the subject, at which the first signal was acquired; and using a magnetic resonance imaging (MRI) scanner, acquiring a set of multiple images at the location indicated by the first signal, over a portion, of a subsequent physiological motion cycle of the subject, that includes the phase indicated by the second signal;

processing, via a processor, the first signal, the second signal and the set of multiple images, the processor defining a scan plane covering a pathway of the intrabody tool, a scan window that covers a portion of the physiological motion cycle that is approximately temporally centered around the phase of the physiological motion cycle at the location and orientation of the intrabody tool, and a number of images to be captured in the scan window, the set of multiple images are captured at various phases within the scan window.

12. The method according to claim 11, wherein the first signal further indicates an orientation of the intrabody tool, and wherein acquiring the set of images comprises acquiring the set of multiple images along the orientation of the intrabody tool.

13. The method according to claim 11, wherein the portion of the subsequent motion cycle is temporally centered on the phase indicated by the second signal.

14. The method according to claim 11, wherein the motion cycle is a cardiac cycle, and the subsequent motion cycle is a subsequent cardiac cycle.

15. The method according to claim 14, wherein the intrabody tool includes an ablation catheter, and wherein acquiring the set of multiple images comprises acquiring the set of images while the ablation catheter is ablating a portion of cardiac tissue.

16. The method according to claim 14, wherein the portion of the subsequent cardiac cycle has a duration of 70-130 ms.

17. The method according to claim 11, wherein the set of multiple images includes between 10 and 20 images.

18. The method according to claim 11, comprising acquiring a plurality of sets of images over, respectively, a plurality of subsequent physiological motion cycles of the subject.

19. The method according to claim 11, further comprising automatically selecting, from the set, a selected image that shows the intrabody tool better than other images of the set, by matching a template image, which shows the intrabody tool, to the set of multiple images.

20. The method according to claim 19, further comprising updating a temperature map, using a phase image that corresponds to the selected image.

* * * * *